(12) United States Patent
Li et al.

(10) Patent No.: US 11,793,846 B2
(45) Date of Patent: Oct. 24, 2023

(54) **BITTER *GANODERMA LUCIDUM* SPORE POWDER AND PREPARATION METHOD THEREOF**

(71) Applicants: Zhejiang Shouxiangu Pharmaceutical Company, Ltd., Zhejiang (CN); Jinhua Shouxiangu Pharmaceutical Co. Ltd, Zhejiang (CN)

(72) Inventors: Zhenhao Li, Zheijiang (CN); Jing Xu, Zhejiang (CN); Ying Wang, Zhejiang (CN); Yuejiao Shi, Zhejiang (CN); Mingyan Li, Zhejiang (CN)

(73) Assignees: Zhejiang Shouxiangu Pharmaceutical Company, Ltd, Zhejiang (CN); Jinhua Shouxiangu Pharmaceutical Co. Ltd, Zhejiang (CN)

( * ) Notice: Subject to any disclaimer, the term of this patent is extended or adjusted under 35 U.S.C. 154(b) by 18 days.

(21) Appl. No.: 17/365,035

(22) Filed: Jul. 1, 2021

(65) Prior Publication Data

US 2021/0322498 A1 Oct. 21, 2021

Related U.S. Application Data

(62) Division of application No. 16/604,213, filed as application No. PCT/CN2018/090414 on Jun. 8, 2018, now Pat. No. 11,083,763.

(30) Foreign Application Priority Data

Oct. 16, 2017 (CN) .......................... 201710958494.8

(51) Int. Cl.
*A61K 36/074* (2006.01)

(52) U.S. Cl.
CPC ........ *A61K 36/074* (2013.01); *A61K 2236/13* (2013.01); *A61K 2236/17* (2013.01); *A61K 2236/331* (2013.01); *A61K 2236/53* (2013.01)

(58) Field of Classification Search
None
See application file for complete search history.

(56) References Cited

FOREIGN PATENT DOCUMENTS

| CN | 1628693 | A | * | 6/2005 |
|---|---|---|---|---|
| CN | 101991615 | A | | 3/2011 |
| CN | 101703531 | B | | 8/2011 |
| CN | 102766593 | A | | 11/2012 |
| CN | 103468628 | B | | 5/2015 |
| CN | 107158043 | A | | 9/2017 |
| CN | 105175564 | B | | 1/2018 |
| CN | 107661360 | A | | 2/2018 |

OTHER PUBLICATIONS

CN-1628693-A translated doc (Year: 2005).*
What is Ganoderma Spore. Ganoderma Lucidum Q & A Center., Aug. 31, 2010 (Aug. 31, 2010), ISSN: 978-7-534, p. 13. Non-official translation Feng, Min et al.
Zhao (Investigation of Ice-Assisted Sonication on the Microstructure and Chemical Quality of Ganoderma lucidum Spores, Journal of Food Science, Aug. 20, 2014) (Year: 2014).

* cited by examiner

*Primary Examiner* — Terry A McKelvey
*Assistant Examiner* — Jacob A Boeckelman
(74) *Attorney, Agent, or Firm* — TROUTMAN PEPPER HAMILTON SANDERS LLP; Christopher C. Close, Jr.

(57) ABSTRACT

Disclosed is a method for preparing bitter *Ganoderma lucidum* spore powder, and relates to the field of drugs or health care products. The method includes: removing visible impurities from *Ganoderma lucidum* spores, conducting ice bath and heating extraction, filtering through a microfiltration membrane, sterilizing by drying, and conducting sporoderm disruption to obtain the bitter *Ganoderma lucidum* spore powder. The preparation method effectively improves the content of the bitter substances in the *Ganoderma lucidum* spore powder by removing shriveled spores through multiple times of impurity removal and filtration in combination with the manner of conducting sporoderm disruption after extraction. Taking the total *Ganoderma lucidum* triterpenoids in the *Ganoderma lucidum* spores as a representative of the bitter substances, the content of the total *Ganoderma lucidum* triterpenoids can reach 5-8%. Meanwhile, the preparation method can also make the content of *Ganoderma lucidum* polysaccharides reaching 6-10%.

4 Claims, 3 Drawing Sheets

Active

BITTER *GANODERMA LUCIDUM* SPORE POWDER AND PREPARATION METHOD THEREOF

This application is a Divisional of U.S. patent application Ser. No. 16/604,213 filed Oct. 10, 2019, which claims the benefit of Chinese Patent Application No. 201710958494.8 filed to the State Intellectual Property Office on Oct. 16, 2017 and entitled "BITTER *GANODERMA LUCIDUM* SPORE POWDER AND PREPARATION METHOD THEREOF", which is incorporated herein by reference in its entirety.

TECHNICAL FIELD

The present invention relates to the field of traditional Chinese medicines, and in particular, to bitter *Ganoderma lucidum* spore powder and a preparation method thereof.

BACKGROUND

*Ganoderma lucidum*, also known as "immortal grass", is of sweet property and mild flavor in traditional Chinese medicine theory, and is a precious medicinal fungus. It is recorded in ancient books such as "Shennong Bencaojing" and "Compendium of Materia Medica" that, *Ganoderma lucidum* has functions such as "enriching the heart-qi" and "acting on heart and nourishing blood", "benefiting the heart and energizing meridians", "relieving uneasiness of mind and body tranquilization", "benefiting pneuma", "strengthening muscles and bones", and is classified as the high grade. The traditional medicinal part of *Ganoderma lucidum* is limited to the fruiting body, namely the sporocarp. *Ganoderma lucidum* spores are microspores that are ejected from the caps at the mature period of *Ganoderma lucidum*, and have all the genetically active components of *Ganoderma lucidum*.

A *Ganoderma lucidum* spore is brown, ovate, flat at one end, sized (8.5-11.2) μm×(5.2-6.9) μm, and have a double-layer sporoderm. Many small acicular protrusions are generated in the brown inner layer of each spore, which extend deeply into a transparent outer layer of the sporoderm, while the outer sporoderm layer is smooth. Since the outer sporoderm of the *Ganoderma lucidum* spore is composed of chitin which is extremely difficult to be digested by gastric acid, it is generally considered that it is difficult for the human body to fully utilize active components inside the *Ganoderma lucidum* spore if the *Ganoderma lucidum* spore has not been subjected to sporoderm disruption.

In recent years, with the development of artificial cultivation techniques and sporoderm disruption techniques, as well as the deepening research on bioactive components, pharmacological effects and processing methods of *Ganoderma lucidum* spores, preparation of *Ganoderma lucidum* spore powder by disrupting the sporoderm of *Ganoderma lucidum* spores becomes an important route to fully use the active components of the *Ganoderma lucidum* spores.

The properties of traditional Chinese medicine include four properties; five flavors; meridian tropism; ascending, descending, sinking and floating; and toxicity. Among them, five flavors refer to sour, bitter, sweet, pungent, and salty. "Plain Questions•Discussion on the Crucial" states: "pungent can cause volatilization and promotes the circulation of Qi; sour can cause astringing and can induce astringency; sweet can alleviate pain and can cause tonifying; bitter can deprive the evil wetness and can discharge the defecation; and salty can soften hardness to dissipate stagnation and cause defecation". That is, the five flavors represent different pharmacological effects. It is believed in traditional Chinese medicine and pharmacy that, the five flavors enter the stomach and respectively act on the five internal organs to nourish the five internal organs. According to clinical evidence, the five flavors are essentially a sign of the taste and efficacy of a drug. A bitter drug has the effects of purgation, discharging fire, calming adverse-rising energy and depriving the evil wetness. It is believed in modern medicine that the traditional Chinese medicine contains many different kinds of active substances, such as alkaloids, glycosides, volatile oils, tannins, resins, organic acids, pigments. Depending on differences in type and contents of organic compounds contained in different traditional Chinese medicines, the traditional Chinese medicine has five flavors, i.e., sour, bitter, sweet, pungent, and salty. Since the various active substances contained in a traditional Chinese medicine interact with one another and affect one another, the main flavors presented by different traditional Chinese medicines are different.

For now, most of the commercially available *Ganoderma lucidum* spore powder has not been found to have the bitter taste of *Ganoderma lucidum* spore powder when being tasted by consumers. This is mainly because the *Ganoderma lucidum* spore powder prepared by the existing preparation method has low contents of bitter substances, which does not reach the bitter taste threshold of a human tongue, and thus cannot give play to effects of the bitter substances contained in *Ganoderma lucidum* spores.

SUMMARY

In view of this, the objective of the present invention is to provide a method for preparing bitter *Ganoderma lucidum* spore powder, which improves the contents of bitter substances of *Ganoderma lucidum* spore powder, and makes the bitter taste of the *Ganoderma lucidum* spore powder obvious.

The present invention provides a method for preparing bitter *Ganoderma lucidum* spore powder, including the following steps:

(1) removing visible impurities from *Ganoderma lucidum* spores;

(2) ice bathing the *Ganoderma lucidum* spores obtained in step (1), then mixing the ice-bathed *Ganoderma lucidum* spores with water, and heating the mixture at 90-100° C. for 1.5-3 h to obtain a suspension of *Ganoderma lucidum* spores;

(3) filtering the suspension of *Ganoderma lucidum* spores obtained in step (2) through a microfiltration membrane, and collecting the filter residue with a particle diameter of more than 5 μm and the filtrate with a particle diameter of less than 1 μm;

(4) mixing the filter residue and filtrate obtained in step (3), and then drying and sterilizing the mixture; and (5) conducting sporoderm disruption of the material sterilized in step (4) to obtain the bitter *Ganoderma lucidum* spore powder.

Preferably, the impurity removal manner of step (1) includes: passing the *Ganoderma lucidum* spores through a 60-120 mesh sieve, mixing the sieved *Ganoderma lucidum* spores with water under stirring, standing to allow stratification, taking and centrifuging the suspension of the intermediate layer to obtain a precipitate, which are the impurity-removed *Ganoderma lucidum* spores.

Preferably, the centrifugation rate of the suspension of the intermediate layer is 800-1,200 rpm.

Preferably, the step of preparing the suspension of the *Ganoderma lucidum* spores described in step (2) is: ice bathing the *Ganoderma lucidum* spores obtained in step (1), then mixing the ice-bathed *Ganoderma lucidum* spores with water, heating the mixture at 90-100° C. for 1.5-3 h, and centrifuging the mixture obtained after the heating to obtain a supernatant and a precipitate; and repeating the ice bathing, heating at 90-100° C., and centrifuging operations on the obtained precipitate, and combining the supernatant obtained from each centrifugation with the mixed solution obtained after the last heating to obtain a suspension of the *Ganoderma lucidum* spores.

Preferably, the number of repetitions is 2-4.

Preferably, the condition for centrifuging the mixed solution is: centrifuging at a rotation speed of 800-1,200 rpm for a time of 15-45 min.

Preferably, the manner of filtering through the microfiltration membrane in step (3) includes: filtering the suspension of *Ganoderma lucidum* spores obtained in step (2) through a 5-6 μm microfiltration membrane to obtain a filtrate and the filter residue with the particle diameter of more than 5 μm; and secondly filtering the filtrate through a microfiltration membrane of 1 μm to obtain the filtrate with the particle diameter of less than 1 μm.

Preferably, the drying of step (4) is spray drying.

Preferably, the sterilizing of step (4) includes: sequentially performing low-pressure sterilization and low-temperature drying on the dried material, where the conditions for the low-pressure sterilization are: a sterilization pressure of 70-80 kPa, a sterilization temperature of 110-120° C., a sterilization time of 25-40 min; and the condition for the low-temperature drying is: drying under normal pressure at 55-65° C.

The present invention further provides bitter *Ganoderma lucidum* spore powder obtained by the preparation method of the above technical solution.

The present invention provides a drug or health care product including the bitter *Ganoderma lucidum* spore powder of the above technical solution, where the drug or health care product has a dosage form selected from granules, tablets, powders, capsules, oral liquids, injections, sprays, aerosols, power aerosols, lotions, liniments, ointments, emulsions, patches, eye drops, nasal drops, suppositories, pills, microsphere preparations, tinctures, sustained release preparations, controlled release preparations or targeting preparations, and the like.

Preferably, the content of the bitter *Ganoderma lucidum* spore powder in the drug or health care product is no less than 80%.

Preferably, the drug or health care product also includes a pharmaceutically acceptable auxiliary material.

Preferably, the pharmaceutically acceptable auxiliary material includes one or more of a pharmaceutically acceptable carrier, a diluent, an adjuvant and an excipient.

Compared with the prior art, the present invention has the following advantages.

The present invention provides a method for preparing bitter *Ganoderma lucidum* spore powder, including: removing an impurity from *Ganoderma lucidum* spores, conducting ice bathing and heating extraction, filtering through a microfiltration membrane, sterilizing at low pressure, and conducting sporoderm disruption to obtain the bitter *Ganoderma lucidum* spore powder. The preparation method provided by the present invention effectively improves the contents of the bitter substances in the *Ganoderma lucidum* spore powder by removing shriveled spores through multiple times of impurity removal and filtration in combination with the manner of conducting sporoderm disruption after extraction. Taking the total *Ganoderma lucidum* triterpenoids in the *Ganoderma lucidum* spores as a representative of the bitter substances, the content of the total *Ganoderma lucidum* triterpenoids can reach 5-8 wt %, while the content of the total *Ganoderma lucidum* triterpenoids prepared by conventional sporoderm disruption is only about 1.7 wt %. Meanwhile, the preparation method provided by the present invention can not only improve the bitter substances contained in the *Ganoderma lucidum* spore powder, but also make the content of *Ganoderma lucidum* polysaccharides reach 6-10 wt %, while the content of the *Ganoderma lucidum* polysaccharides in the conventional sporoderm-disrupted *Ganoderma lucidum* spore powder is only about 0.9 wt %. The method for preparing the bitter *Ganoderma lucidum* spore powder of the present invention has a sporoderm disruption rate which can reach over 95%.

*Ganoderma lucidum* spore raw materials contain certain shriveled spores. These shriveled spores have low plumpness and a low content of active substances, and it is difficult to release the active ingredients inside them even after they are subjected to processing. This is the main reason that most of the commercially available *Ganoderma lucidum* spore powder in the market have no bitter taste and a low content of bitter substances. The method for preparing bitter *Ganoderma lucidum* spore powder provided by the present invention removes the shriveled spores with low plumpness through multiple times of impurity removal and filtration and thus screens out the *Ganoderma lucidum* spores with high plumpness for preparation, so that the active substances are more easily enriched and the impurities in the bitter *Ganoderma lucidum* spore powder is reduced, improving extraction efficiency while reducing a production cost.

Also, the shriveled spores in the *Ganoderma lucidum* spore raw materials are mostly mildewed and rotted. It is difficult to remove the shriveled spores in large quantities by the preparation method of *Ganoderma lucidum* spore powder in the prior art, so that the mildewed and rotted shriveled spores contaminate other raw materials, resulting in that the microbial content of the *Ganoderma lucidum* spore powder exceeds the limit of oral drugs. In the present invention, by processing through continuous heating sterilization, sterilization by microfiltration membrane filtration and low-pressure sterilization, it is ensured that the microbial limit of the bitter *Ganoderma lucidum* spore powder obtained after sporoderm disruption meets relevant standards of drugs or health care products since the shriveled spores are removed.

The method for preparing bitter *Ganoderma lucidum* spore powder provided by the present invention extract the bitter substances from the *Ganoderma lucidum* spores by adopting the manner of first extracting and then conducting sporoderm disruption, where the *Ganoderma lucidum* spores subjected to impurity removal are ice bathed during extraction, and then heated at 90-100° C., such that the *Ganoderma lucidum* spores rapidly expand after being stimulated by alternate cooling and heating, to release the active components such as the bitter substances through the micropores on surfaces of the *Ganoderma lucidum* spores, thereby improving the content of active substances and extraction rate of the bitter *Ganoderma lucidum* spore powder.

In some specific embodiments of the present invention, foreign matters with relatively large particle sizes, and sediments are removed by the two steps including sieving and then adding water for settling stratification, and centrifuging the suspension of the intermediate layer, but the two steps can only remove a small part of the shriveled spores;

and in combination with the step of conducting microfiltration membrane filtration twice, these shriveled spores with particle sizes of 1-5 μm can be effectively removed. That is, the preparation method provided by the present invention effectively removes large particle impurities and most of the shriveled spores from the *Ganoderma lucidum* spore raw material by multiple times of impurity removal.

The method for preparing bitter *Ganoderma lucidum* spore powder provided by the present invention removes microorganisms by the manner of alternating multiple times of impurity removal, filtration and low-pressure sterilization, so that the prepared bitter *Ganoderma lucidum* spore powder has a low microbial content and meets the standards of oral drugs, and thus is safe and reliable.

The present invention further provides bitter *Ganoderma lucidum* spore powder prepared by the above preparation method. During storage, the bitter *Ganoderma lucidum* spore powder obtained by using the preparation method provided by the present invention is more resistant to oxidative deterioration with the peroxide value not exceeding a limit. This is mainly caused by two reasons, where firstly, the *Ganoderma lucidum* spore powder contains relatively oil and grease components including saturated fatty acids and unsaturated fatty acids. The oil and grease components are matured after being heated at 90-100° C., and it is difficult to continually oxidize the matured oil and grease components, thereby overcoming the problem that a peroxide value exceeds the limit since the *Ganoderma lucidum* spore powder obtained by a conventional technology is sustainable to oxidative sour rot during storage due to the un-matured oil and grease components; and secondly, by using the preparation method provided by the present invention, the microorganisms can be effectively inactivated before sporoderm disruption, thereby preventing increase of the peroxide value caused by microbial oxidation of active substances.

Moreover, the bitter *Ganoderma lucidum* spore powder of the present invention can be orally administered directly, as the microbial content which meets the standards of oral drugs. The *Ganoderma lucidum* spore powder is safe and reliable, and has an obvious bitter taste.

A drug or health care product including the bitter *Ganoderma lucidum* spore powder of the present invention can be directly administered, or can be prepared into various dosage forms, such as granules, tablets, powders, capsules, oral liquids, injections, sprays, aerosols, power aerosols, lotions, liniments, ointments, emulsions, patches, eye drops, nasal drops, suppositories, pills, microsphere preparations, tinctures, sustained release preparations, controlled release preparations or targeting preparations, and the like. In particular, the tablets include, but not limited to, sugar-coated tablets, film-coated tablets, enteric coated tablets, buccal tablets, and the like; and the capsules include, but not limited to, hard capsules, soft capsules, and the like.

In the present invention, the drug or health care product containing the bitter *Ganoderma lucidum* spore powder further includes a pharmaceutically acceptable auxiliary material, where the pharmaceutically acceptable auxiliary material includes, but not limited to one or more of a pharmaceutically acceptable carrier, a diluent, an adjuvant and an excipient. The pharmaceutically acceptable carrier includes, but not limited to, a liposome, an ethosome, a polymer micelle, a nanostructured lipid carrier, a solid lipid nanocarrier, a mesoporous silica nanoparticle, etc.; the pharmaceutically acceptable auxiliary material, such as the diluent, the adjuvant, the excipient and the like, may particularly include a pharmaceutically acceptable preservative, antioxidant, filler, disintegrant, hemectant, emulsifier, suspension agent, solvent, dispersion medium, coating, antibacterial agent or isotonic agent and absorption delaying agent, etc.

In particular, the disintegrant includes, but not limited to, one or more of a dry starch, sodium carboxymethyl starch, low-substituted hydroxypropyl cellulose, cross-linked polyvinylpyrrolidone, effervescent disintegrant, and croscarmellose sodium. The filler includes, but not limited to, one or more of a microcrystalline cellulose, pregelatinized starch, hydroxypropyl cellulose, and polyethylene glycol. The diluting agent includes, but not limited to, one or more of lactose, starch, dextrin, inorganic salt diluents, and mannitol. The binder includes, but not limited to, one or more of ethanol, a sugar syrup, a starch slurry, polyvinylpyrrolidone, a cellulose derivative, a mucilage, and dextrin. The pharmaceutical carrier includes, but not limited to, a liposome, an ethosome, a polymer micelle, a nanostructured lipid carrier, a solid lipid nanocarrier, a mesoporous silica nanoparticle, etc.

DETAILED DESCRIPTION

Figure 1:
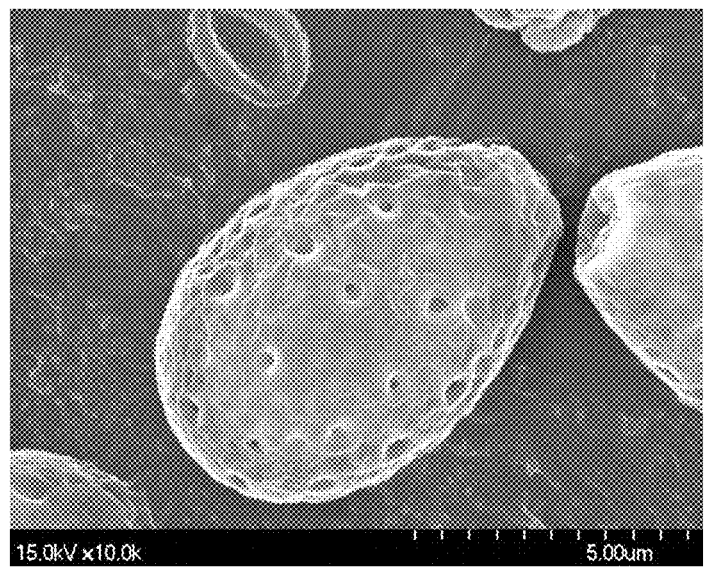
FIG. 1 is a scanning electron micrograph of *Ganoderma lucidum* spores.

The present invention is further described below with reference to the accompanying drawings and embodiments.

The present invention provides a method for preparing bitter *Ganoderma lucidum* spore powder, including the following steps:

(1) removing visible impurities from *Ganoderma lucidum* spores;

(2) ice bathing the *Ganoderma lucidum* spores obtained in step (1), then mixing the ice-bathed *Ganoderma lucidum* spores with water, and heating the mixture at 90-100° C. for 1.5-3 h to obtain a suspension of *Ganoderma lucidum* spores;

(3) filtering the suspension of *Ganoderma lucidum* spores obtained in step (2) through a microfiltration membrane, and collecting the filter residue with a particle diameter of more than 5 μm and the filtrate with a particle diameter of less than 1 μm;

(4) mixing the filter residue and filtrate obtained in step (3), and then drying and sterilizing the mixture; and (5) conducting sporoderm disruption of the material sterilized in step (4) to obtain the bitter *Ganoderma lucidum* spore powder.

In the present invention, the raw material used for preparing the bitter *Ganoderma lucidum* spore powder is an untreated *Ganoderma lucidum* spore raw material. The present invention has no particular limitation on the source of the *Ganoderma lucidum* spore raw material, and a commercially available product can be used.

In the present invention, firstly the impurities are removed from the *Ganoderma lucidum* spore powder, i.e., removing the sediments incorporated into the *Ganoderma lucidum* spore raw material and the shriveled spores. The impurity removal method of the present invention includes: passing the *Ganoderma lucidum* spores through a 60-120 mesh sieve, mixing the sieved *Ganoderma lucidum* spores with water under stirring, standing to allow stratification, taking and centrifuging the suspension of the intermediate layer to obtain a precipitate, which is the *Ganoderma lucidum* spores after being subjected to impurity removal.

Preferably, when the *Ganoderma lucidum* spores passing through the sieve have a particle size of 60 mesh, the sieving efficiency is higher and suitable for large-scale production; and when the *Ganoderma lucidum* spores passing through the sieve have a particle size of 100 mesh, the sieving efficiency is relatively lower than that of 60 mesh, but the impurity removal efficiency is better.

In the present invention, the sieved *Ganoderma lucidum* spores are mixed with water under stirring in a mass to volume ratio of 1:5-12 into a suspension for settling stratification. Preferably, the mass to volume ratio is 1:10. In the present invention, the mass and the volume are of the same order of magnitude. The stirring time is preferably 15-35 min; and more preferably 20 min. The standing time is preferably 10-30 min; and more preferably 15 min. Since the sediments, shriveled spores and *Ganoderma lucidum* spores with high plumpness have different buoyancy in water, so the solution after settling stratification is divided into three layers, i.e., the upper, intermediate and lower layers. The upper layer is the shriveled spores with low plumpness, the lower layer is the sediments, and the intermediate layer is a suspension of the *Ganoderma lucidum* spores with relatively higher plumpness.

In the present invention, the centrifugation condition of the suspension of the intermediate layer is: centrifuging at a centrifugation rate of 800-1200 rpm for 15-45 min. The centrifugation rate is preferably 1,000 rpm. The centrifugation time is preferably 40 min.

In the present invention, after the impurity is removed from the *Ganoderma lucidum* spores, ice bath the *Ganoderma lucidum* spores, and then the ice-bathed *Ganoderma lucidum* spores are mixed with water, and heated at 90-100° C. for 1.5-3 h to obtain a suspension of the *Ganoderma lucidum* spores. The ice bathing time is preferably 20-50 min; and more preferably 40 min. In the present invention, the ice bathing temperature is 0-4° C., i.e., the temperature of an ice-water mixture.

Specifically, the step of preparing the suspension of the *Ganoderma lucidum* spores described in step (2) is: ice bathing the *Ganoderma lucidum* spores obtained in step (1), then mixing the ice-bathed *Ganoderma lucidum* spores with water, heating the mixture at 90-100° C. for 1.5-3 h, and centrifuging the mixture obtained after the heating to obtain a supernatant and a precipitate; and repeating the ice bathing, heating at 90-100° C., and centrifuging operations on the obtained precipitate, and combining the supernatant obtained from each centrifugation with the mixed solution obtained after the last heating to obtain a suspension of the *Ganoderma lucidum* spores.

The mass to volume ratio of the ice-bathed *Ganoderma lucidum* spores to water in the present invention is 1:2-12; and more preferably 1:5-10. The heating time of the present invention is preferably 2 h. The heating temperature is preferably 100° C. In the present invention, the mass and the volume are of the same order of magnitude.

In the present invention, the number of repetitions is preferably 2-4, and more preferably 3. Repeating the step of ice bathing and heating can further increase the extraction rate of the active substances and increase the content of the bitter substances in the bitter *Ganoderma lucidum* spore powder.

As described in the present invention, the condition for centrifuging the mixed solution to obtain the suspension of the *Ganoderma lucidum* spores is preferably: centrifuging at a rotation speed of 800-1,200 rpm for a time of 15-45 min. The centrifugal rotation speed is more preferably 1,000 rpm. The centrifugation time is more preferably 30 min.

Figure 2:
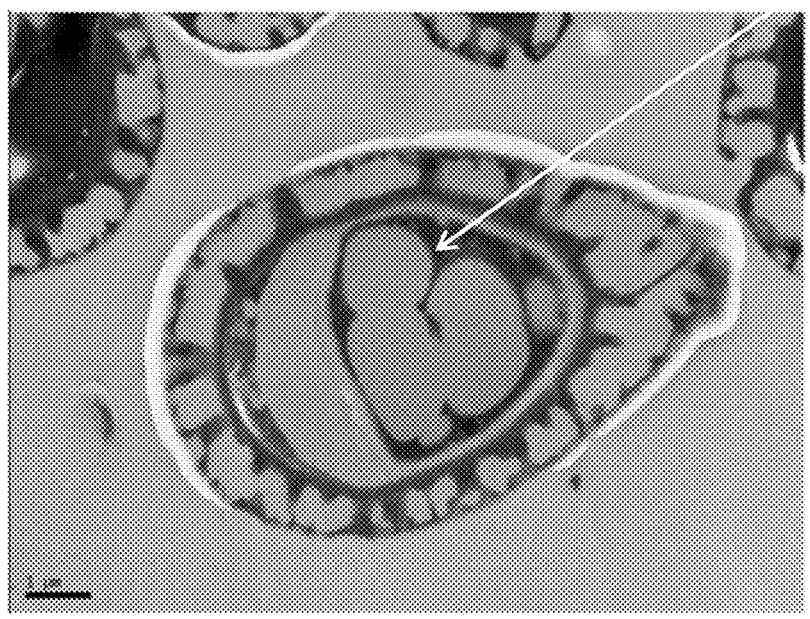
FIG. 2 is a longitudinal cut diagram of the *Ganoderma lucidum* spores.

As shown in FIG. 1, a plumped *Ganoderma lucidum* spore is egg-shaped and has a size of 6-11 μm in length and 4-7 μm in width. The surface of the *Ganoderma lucidum* spore has a microporous structure. In the longitudinal cut diagram of the *Ganoderma lucidum* spores as shown in FIG. 2, the active components of the *Ganoderma lucidum* spores are mainly present in a cystic cavity surrounded by the sporoderm. The preparation method provided by the present invention sequentially performs ice bathing and heating on the *Ganoderma lucidum* spores, such that the *Ganoderma lucidum* spores rapidly expand through simulation by alternate cooling and heating. During the rapid warming process, the micropores on the surfaces of the *Ganoderma lucidum* spores are expanded to release the active substances inside the *Ganoderma lucidum* spores through the micropores, so that the active components such as the bitter substances in the *Ganoderma lucidum* spores are extracted.

At the same time, the preparation method of the present invention can also kill part of microorganisms by performing ice bathing and heating on the impurity-removed *Ganoderma lucidum* spore powder, thereby playing a role of sterilization.

In the present invention, the obtained suspension of *Ganoderma lucidum* spores is filtered through the microfiltration membrane, and the filter residue with the particle diameter of more than 5 μm and the filtrate with the particle diameter of less than 1 μm are collected. In the present invention, the manner of filtering through the microfiltration membrane particularly includes: filtering the suspension of *Ganoderma lucidum* spores through a 5-6 μm microfiltration membrane to obtain a filtrate and the filter residue with the particle diameter of more than 5 μm; and secondly filtering the filtrate through a microfiltration membrane of 1 μm to obtain the filtrate with the particle diameter of less than 1 μm. The specification of the microfiltration membrane for collecting the filter residue with the particle diameter of more than 5 μm is preferably 5 μm. The present invention realizes removal of a mass of shriveled spores from the *Ganoderma lucidum* spores by twice microfiltration membrane filtration, effectively improving the quality of the *Ganoderma lucidum* spores for subsequent processing.

According to the difference in particle size between the plumped *Ganoderma lucidum* spores and the shriveled spores, the present invention removes the shriveled spores having a particle size of 1-5 μm through microfiltration membrane filtration, and the remaining filter residue is the plumped *Ganoderma lucidum* spores, thereby further improving the quality of the *Ganoderma lucidum* spores. In the present invention, the *Ganoderma lucidum* spores are firstly subjected to extraction through alternate cooling and heating, and then subjected to removal of shriveled spores, where since the extraction manner of alternate cooling and heating can also release part of active components from the shriveled spores, but it is difficult to obtain the active substances contained in the shriveled spores through the subsequent sporoderm disruption. The separation of most of the shriveled spores before the sporoderm disruption can save the processing cost of subsequent steps.

Figure 3:
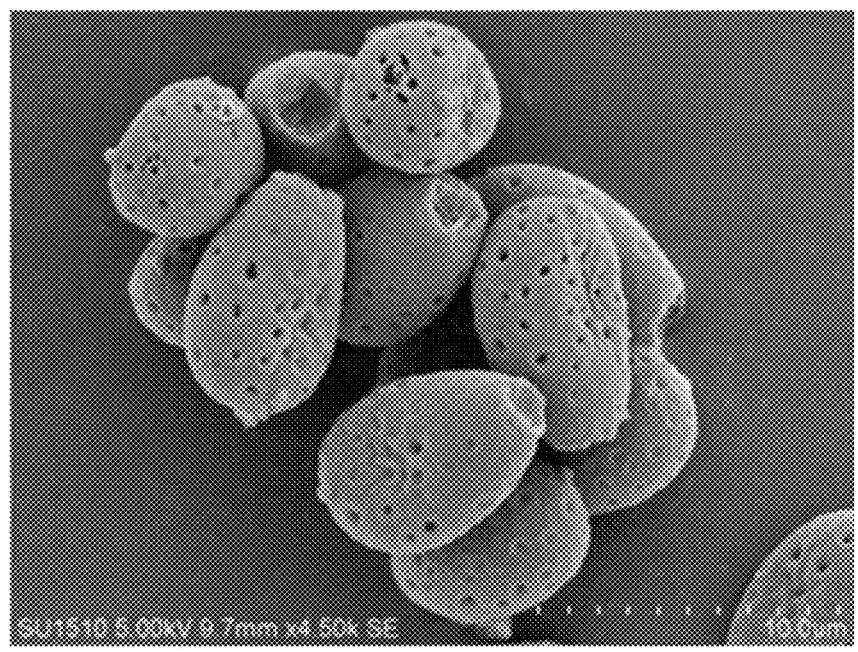
FIG. 3 is a scanning micrograph of shriveled spores of the *Ganoderma lucidum* spores.

The harvesting period of the *Ganoderma lucidum* spore raw material is from July to October, which is a long-time span with humid and muggy climate, and thus is easy to cause microbial infection of spores, resulting in the decline of plumpness of the *Ganoderma lucidum* spores and the formation of shriveled spores. As shown in FIG. 3, the shriveled spores in these *Ganoderma lucidum* spores have low plumpness, are mostly rotted and mildewed, and have low contents of active substances. Therefore it is difficult to release the active components inside the shriveled spores even upon a conventional sporoderm disruption process. The preparation method provided by the present invention improves the quality of the raw material by removing the shriveled spores with low plumpness by means of impurity removal and filtration. Processing *Ganoderma lucidum* spore raw materials of different sources by the method for preparing bitter *Ganoderma lucidum* spore powder as provided by the present invention can significantly improve the content of the bitter substances in the *Ganoderma lucidum* spore powder.

In the present invention, the filter residue with the particle diameter of more than 5 μm and the filtrate with the particle diameter of less than 1 μm obtained through microfiltration membrane filtration are mixed, dried, and sterilized. In the present invention, preferably the mixture of the filter residue and the filtrate is subjected to concentration before the drying; and the concentration is more preferably concentration under reduced pressure. The concentration is more preferably concentrating to 1/10-1/20 of the original volume; and most preferably concentrating to 1/15 of the original volume.

The drying of the present invention is preferably spray drying. The conditions for the spray drying are preferably: an air inlet temperature of 170-195° C.; and preferably 190° C. The air outlet temperature is 90-105° C.; and preferably 100° C. The feed frequency is 70-80 rpm; and preferably 75 rpm. The negative pressure in the tower is 0.2-0.3 MPa; and preferably 0.25 MPa. The rotational speed of an atomizer is 350-450 rpm; and preferably 400 rpm. The moisture content of the material obtained after drying is <7%; and more preferably, the moisture content is 2-5%.

The sterilization according to the present invention includes the steps of low-pressure sterilization and low-temperature drying, and the conditions for the low-pressure sterilization of the present invention are preferably: a sterilization pressure of 70-80 kPa; and more preferably 75 KPa. The sterilization temperature is 110-120° C.; and more preferably 115° C. The sterilization time is 25-40 min; and more preferably 30 min. The drying temperature of the low-temperature drying is preferably 55-65° C.; and more preferably 60° C. The time of the low-temperature drying is preferably 60-100 min; and more preferably 90 min.

The present invention conducts sterilization by means of a combination of low-pressure sterilization and low-temperature drying. The manner of low-pressure sterilization can protect activities of active substances such as polysaccharides, and conducting the low-temperature drying after the low-pressure sterilization can make up the problem of incomplete sterilization probably occurring in the low-pressure sterilization.

The microbial limit of the bitter *Ganoderma lucidum* spore powder obtained by the preparation method provided by the present invention meets the standards of oral drugs. That is, the total number of aerobic bacteria is less than $10^3$ cfu/g, and the total number of molds and yeasts is less than $10^2$ cfu/g, no *Salmonella* (10 g) is detected, and the number of bile-resistant Gram-negative bacteria is less than $10^4$ cfu/g. The bitter *Ganoderma lucidum* spore powder obtained by the preparation method provided by the present invention is safe and reliable in quality, and can be directly used for preparing oral traditional Chinese medicine decoction pieces without any further sterilization process, preventing loss of the active components due to the sterilization operation.

In the present invention, after the sterilized material is obtained, the material is subjected to sporoderm disruption to obtain the bitter *Ganoderma lucidum* spore powder. The sporoderm disruption method is preferably an enzymatic hydrolysis method, an acid hydrolysis method, an alkali hydrolysis method, an ultrasonic method or a mechanical method; and more preferably, conducting sporoderm disruption through the mechanical method. In particular, the sporoderm disruption through the mechanical method is that the sterilized material is subjected to sporoderm disruption through repeated extruding; and the number of repetitions is preferably 16-20 times; and more preferably 18 times. The preparation method of the present invention has a final sporoderm disruption rate which can reach over 95%. Preferably, the present invention conducts sporoderm disruption by using a shear mill.

The present invention further provides bitter *Ganoderma lucidum* spore powder prepared by the above preparation method, where the content of the *Ganoderma lucidum* triterpenes in the bitter *Ganoderma lucidum* spore powder is no less than 5%, and the content of the *Ganoderma lucidum* polysaccharides is no less than 6%.

The present invention further provides a drug or health care product containing the bitter *Ganoderma lucidum* spore powder described in the above technical solution, including the bitter *Ganoderma lucidum* spore powder obtained by the preparation method described in the above technical solution. Preferably, the mass percent of the bitter *Ganoderma lucidum* spore powder in the drug or health care product is no less than 80%; and more preferably no less than 85%.

In the present invention, the dosage form of the bitter *Ganoderma lucidum* spore powder drug or health care product includes, but not limited to, powder, tablets, granules or capsules. In the present invention, the bitter *Ganoderma lucidum* spore powder drug or health care product further includes a pharmaceutically acceptable auxiliary material, which includes, but not limited to, one or more of a binder, a dispersing agent or a filler. The binder is preferably water or an ethanol solution.

The drug or health care product including the bitter *Ganoderma lucidum* spore powder as provided by the present invention can be orally administered directly, and meets the relevant standards of oral drugs or health care products, and has an obvious bitter taste.

The technical solutions in the present invention will be clearly and completely described below in conjunction with the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

Embodiment 1

A *Ganoderma lucidum* spore raw material was used and passed through a 60 mesh sieve, and the sieved *Ganoderma*

*lucidum* spores were mixed with water at a mass to volume ratio of 1:5, stirred for 20 min, and allowed to stand for 15 min; the intermediate suspension formed after standing was taken, and the suspension of the intermediate layer formed after standing was taken and centrifuged at 1,000 rpm for 20 min; and then the precipitate was taken as the impurity-removed *Ganoderma lucidum* spores.

The impurity-removed *Ganoderma lucidum* spores were ice bathed for 30 min, and then the ice-bathed *Ganoderma lucidum* spores were mixed with water at 100° C. in a mass to volume ratio of 1:5, and heated at 100° C. for 2.5 h; the mixed solution obtained after heating was centrifuged at 1,000 rpm for 20 min to obtain a supernatant and a precipitate; the above operations were repeated for 2 times, and in the last time of repetition the mixture was not centrifuged after heating. The supernatants obtained from each centrifugation and the mixture obtained after heating in the last time of repetition were combined to obtain a suspension of *Ganoderma lucidum* spores.

The suspension of *Ganoderma lucidum* spores was filtered through a microfiltration membrane of 5 μm to obtain a filtrate and the filter residue with the particle diameter of more than 5 μm; and secondly the obtained filtrate was filtered through a microfiltration membrane of 1 μm to obtain the filtrate with the particle diameter of less than 1 μm. The filter residue with the particle diameter of more than 5 μm and the filtrate with the particle diameter of less than 1 μm were mixed, and concentrated under reduced pressure to 1/10 of the original volume, followed by spray drying. The parameters of the spray dryer were: an inlet air temperature of 170° C., an outlet air temperature of 100° C., a feed frequency of 75 rpm, a negative pressure of 0.25 MPa in the tower, and a rotating speed of atomizer of 400 rpm. A dry powder was obtained.

The obtained dry powder was sterilized at a working pressure of 75 KPa and a sterilization temperature of 115° C. for 30 min, and then dried at 60° C. for 60 min to obtain a sterilized material.

The sterilized material was subjected to sporoderm disruption through repeated extruding for 20 times to obtain the bitter *Ganoderma lucidum* spore powder. The sporoderm disruption rate was above 95%.

Embodiment 2

A *Ganoderma lucidum* spore raw material was used and passed through a 100 mesh sieve, and the sieved *Ganoderma lucidum* spores were mixed with water at a mass to volume ratio of 1:10, stirred for 20 min, and allowed to stand for 15 min; the intermediate suspension formed after standing was taken, and the suspension of the intermediate layer formed after standing was taken and centrifuged at 1,000 rpm for 40 min; and then the precipitate was taken as the impurity-removed *Ganoderma lucidum* spores.

The impurity-removed *Ganoderma lucidum* spores were ice bathed for 50 min, and then the ice-bathed *Ganoderma lucidum* spores were mixed with water at 100° C. according to a mass to volume ratio of 1:10, and heated at 100° C. for 3 h; the mixed solution obtained after heating was centrifuged at 1,000 rpm for 20 min to obtain a supernatant and a precipitate; the above operations were repeated for 3 times, and in the last time of repetition the mixture was not centrifuged after heating. The supernatants obtained from each centrifugation and the mixture obtained after heating in the last time of repetition were combined to obtain a suspension of *Ganoderma lucidum* spores.

The suspension of *Ganoderma lucidum* spores was filtered through a microfiltration membrane of 5 μm to obtain a filtrate and the filter residue with the particle diameter of more than 5 μm; and secondly the obtained filtrate was filtered through a microfiltration membrane of 1 μm to obtain the filtrate with the particle diameter of less than 1 μm. The filter residue with the particle diameter of more than 5 μm and the filtrate with the particle diameter of less than 1 μm were mixed, and concentrated under reduced pressure to 1/10 of the original volume, followed by spray drying. The parameters of the spray dryer were: an inlet air temperature of 190° C., an outlet air temperature of 105° C., a feed frequency of 75 rpm, a negative pressure of 0.25 MPa in the tower, and a rotating speed of atomizer of 400 rpm. A dry powder was obtained.

The obtained dry powder was sterilized at a working pressure of 75 KPa and a sterilization temperature of 115° C. for 30 min, and then dried at 60° C. for 60 min to obtain a sterilized material.

The sterilized material was subjected to sporoderm disruption through repeated extruding for 18 times to obtain the bitter *Ganoderma lucidum* spore powder. The sporoderm disruption rate was above 95%.

Embodiment 3

A *Ganoderma lucidum* spore raw material was used and passed through a 100 mesh sieve, and the sieved *Ganoderma lucidum* spores were mixed with water at a mass to volume ratio of 1:10, stirred for 20 min, and allowed to stand for 15 min; the intermediate suspension formed after standing was taken, and the suspension of the intermediate layer formed after standing was taken and centrifuged at 1,000 rpm for 40 min; and then the precipitate was taken as the impurity-removed *Ganoderma lucidum* spores.

The impurity-removed *Ganoderma lucidum* spores were ice bathed for 50 min, and then the ice-bathed *Ganoderma lucidum* spores were mixed with water at 100° C. according to a mass to volume ratio of 1:10, and heated at 100° C. for 3 h; the mixed solution obtained after heating was centrifuged at 1,000 rpm for 20 min to obtain a supernatant and a precipitate; the above operations were repeated for 2 times, and in the last time of repetition the mixture was not centrifuged after heating. The supernatants obtained from each centrifugation and the mixture obtained after heating in the last time of repetition were combined to obtain a suspension of *Ganoderma lucidum* spores.

The suspension of *Ganoderma lucidum* spores was filtered through a microfiltration membrane of 5 μm to obtain a filtrate and the filter residue with the particle diameter of more than 5 μm; and secondly the obtained filtrate was filtered through a microfiltration membrane of 1 μm to obtain the filtrate with the particle diameter of less than 1 μm. The filter residue with the particle diameter of more than 5 μm and the filtrate with the particle diameter of less than 1 μm were mixed, and concentrated under reduced pressure to 1/10 of the original volume, followed by spray drying. The parameters of the spray dryer were: an inlet air temperature of 190° C., an outlet air temperature of 105° C., a feed frequency of 75 rpm, a negative pressure of 0.25 MPa in the tower, and a rotating speed of atomizer of 400 rpm. A dry powder was obtained.

The obtained dry powder was sterilized at a working pressure of 75 KPa and a sterilization temperature of 115° C. for 30 min, and then dried at 60° C. for 90 min to obtain a sterilized material.

The sterilized material was subjected to sporoderm disruption through repeated extruding for 18 times to obtain the bitter *Ganoderma lucidum* spore powder. The sporoderm disruption rate was above 95%.

Embodiment 4

*Ganoderma lucidum* total triterpenes is a kind of typical bitter substances. By taking the *Ganoderma lucidum* total triterpenes as a representative of the bitter substances of the *Ganoderma lucidum* spores, the effect of the preparation method provided by the present invention on the content of the bitter substance is observed. At the same time, by taking *Ganoderma lucidum* polysaccharides as a representative of the active substances, the effect of the preparation method provided by the present invention on the content of other active substances of the *Ganoderma lucidum* spores was observed.

In accordance with the provisions of "Chinese Pharmacopoeia" (2015 edition), the contents of the *Ganoderma lucidum* total triterpenes (with oleanolic acid as the reference) and the *Ganoderma lucidum* polysaccharides (with glucose as the reference) in the *Ganoderma lucidum* spore powder prepared in Embodiments 1-3 were measured. The results are shown in Table 1:

TABLE 1

Contents of Ganoderma Lucidum Total Triterpenes and Ganoderma Lucidum Polysaccharides in the bitter Ganoderma lucidum spore powder

|  | Ganoderma Lucidum Total Triterpenes | Ganoderma Lucidum Polysaccharides |
| --- | --- | --- |
| Embodiment 1 | 6.3% | 7.8% |
| Embodiment 2 | 7.2% | 8.5% |
| Embodiment 3 | 7.4% | 8.9% |

As shown in Table 1, the content of the *Ganoderma lucidum* total triterpenes in the bitter *Ganoderma lucidum* spore powder prepared in Embodiments 1-3 can reach 6.3%-7.4%, while the content of the *Ganoderma lucidum* total triterpenes in the bitter *Ganoderma lucidum* spore powder obtained by the conventional sporoderm disruption method is only about 1.7%, indicating that the preparation method provided by the present invention can significantly increase the content of the *Ganoderma lucidum* total triterpenes in the bitter *Ganoderma lucidum* spore powder.

As shown in Table 1, the content of the *Ganoderma lucidum* polysaccharides in the bitter *Ganoderma lucidum* spore powder prepared in Embodiments 1-3 can reach 7.8-8.9%, while the content of the *Ganoderma lucidum* polysaccharides in the bitter *Ganoderma lucidum* spore powder obtained by the conventional sporoderm disruption method is only about 0.9%, indicating that the preparation method provided by the present invention can significantly increase the content of the *Ganoderma lucidum* polysaccharides in the bitter *Ganoderma lucidum* spore powder.

It can be seen that, the contents of the *Ganoderma lucidum* total triterpenes and the *Ganoderma lucidum* polysaccharides can be significantly increased by using the preparation method provided by the present invention, and it can be further know that the preparation method provided by the present invention can effectively enrich the bitter substances represented by the *Ganoderma lucidum* total triterpenes and other active components represented by the *Ganoderma lucidum* polysaccharides, thereby obtaining bitter *Ganoderma lucidum* spore powder having a distinct bitter taste and a high content of active substances.

Embodiment 6

The bitter *Ganoderma lucidum* spore powder prepared in Embodiment 1 was taken and packaged in a polyethylene composite film to prepare powder having a specification of 0.5-3 g/bag, which are traditional Chinese medicine decoction pieces of the bitter *Ganoderma lucidum* spore powder.

Embodiment 7

100 parts by weight of the bitter *Ganoderma lucidum* spore powder prepared in Embodiment 2 and 25-30 parts by weight of a binder were used as raw materials to further conduct one-step granulation in a fluidized-bed granulator. The binder was an ethanol solution with a mass percentage of 75%.

The parameters of the fluidized-bed granulator were set as: an air volume of 75 m$^3$/h, a liquid supply speed of 10 rpm, atomization pressure of 1.2 bar, and an inlet air temperature of 65° C. The prepared granules were subpackaged in respective polyethylene composite film packages to prepare granules having a specification of 0.5-3 g/bag, which were formula granules of the bitter *Ganoderma lucidum* spore powder.

Embodiment 8

The bitter *Ganoderma lucidum* spore powder prepared in Embodiment 3 was taken and directly compressed, and then packaged in polyethylene composite film packages to obtain tablets having a specification of 0.5-3 g/tablet, which were tablets of the bitter *Ganoderma lucidum* spore powder.

Embodiment 9

The microbial limits of the bitter *Ganoderma lucidum* spore powder obtained in Embodiments 1-3, and the drugs containing the bitter *Ganoderma lucidum* spore powder obtained in Embodiments 6-8, are tested according to the standards on the *Ganoderma lucidum* spore powder according to "Zhejiang Provincial Standards of Processing Traditional Chinese medicine", and according to the relevant microbiological examination methods recited in the Chinese Pharmacopoeia (2015 edition)

The results showed that, the microbial limits of the bitter *Ganoderma lucidum* spore powder obtained in Embodiments 1-3, and the microbial limits of the traditional Chinese medicine decoction pieces of the bitter *Ganoderma lucidum* spore powder, the formula granules and tablets of the bitter *Ganoderma lucidum* spore powder obtained in Embodiments 6-8 all met the standard that the total number of aerobic bacteria should be less than $10^3$ cfu/g, the total number of molds and yeasts should be less than $10^2$ cfu/g, no *Salmonella* (10 g) should be detected. and the number of bile-resistant Gram-negative bacteria should be less than $10^4$ cfu/(1 g). It can be seen that, the preparation method provided by the present invention can directly obtain the bitter *Ganoderma lucidum* spore powder which has a microbial limit meeting the standards and a drug containing the bitter *Ganoderma lucidum* spore powder as prepared therefrom.

Comparative Embodiment 1

A *Ganoderma lucidum* spore raw material was used and passed through a 60 mesh sieve, and the sieved *Ganoderma*

*lucidum* spores were mixed with water at a mass to volume ratio of 1:5, stirred for 20 min, and allowed to stand for 15 min; the intermediate suspension formed after standing was taken, and the suspension of the intermediate layer formed after standing was taken and centrifuged at 1,000 rpm for 20 min; and then the precipitate was taken as the impurity-removed *Ganoderma lucidum* spores.

The impurity-removed *Ganoderma lucidum* spores were dried at 65° C. for 2 h, and the dried *Ganoderma lucidum* spores were subjected to sporoderm disruption through repeated extruding for 20 times to obtain the conventional *Ganoderma lucidum* spore powder.

Embodiment 10

The test of this embodiment verified that, the *Ganoderma lucidum* spore powder obtained by the preparation method as provided by the present invention is more stable during storage than that of the conventional sporoderm disruption method.

According to the standard relating to the acceleration test in Part IV 9001 "Test guidelines for pharmaceutical raw materials and formulation stability" of "Chinese Pharmacopoeia" (2015 edition), and according to the rancidity test methods in "Chinese Pharmacopoeia" (2015 edition), the conventional sporoderm-disrupted *Ganoderma lucidum* spore powder of the Comparative Embodiment 1 and the bitter *Ganoderma lucidum* spore powder prepared by the preparation method provided by the present invention were tested for peroxide values. In the acceleration test, the test temperature was 40° C.±2° C., and the humidity was 75%±5%.

The results were as follows:

TABLE 2

Peroxide value of the bitter and conventional Ganoderma lucidum spore powder during the accelerated test

| Sample | Items | 0 | 1 | 2 months | 3 months | 6 months |
|---|---|---|---|---|---|---|
| Comparative 1 | Peroxide Value | 0.025% | 0.085% | 0.146% | 0.197% | 0.326% |
| Embodiment 1 | | 0.025% | 0.028% | 0.028% | 0.025% | 0.026% |

It could be seen from Table 2 that, the peroxide value of the bitter *Ganoderma lucidum* spore powder obtained in Embodiment 1 had no significant change during the acceleration test; while the conventional sporoderm-disrupted *Ganoderma lucidum* spore powder of the Comparative Embodiment 1 had a peroxide value which was significantly elevated along with increasing of the storage time, and thus had relatively poorer storage stability. It can be seen that, the preparation method provided by the present invention can improve the capability of resistance to oxidative sour rot of the bitter *Ganoderma lucidum* spore powder and improve the storage stability.

Embodiment 11

The test of this embodiment verified that, the preparation method provided by the present invention has the ability of enriching the bitter substances compared with the conventional sporoderm disruption method.

1. Sample preparation: *Ganoderma lucidum* spores No. 1 and *Ganoderma lucidum* spores No. 2 were respectively taken as raw materials for preparation, and the raw materials for preparation were divided into 6 parts in equal amounts, and were processed according to the following description into 6 groups of samples:

Bitter *Ganoderma lucidum* spore powder No. 1 and bitter *Ganoderma lucidum* spore powder No. 2 were prepared according to the preparation method described in Embodiment 1; sporoderm-disrupted anoderma lucidum spore powder No. 1 and sporoderm-disrupted anoderma lucidum spore powder No. 2 were prepared according to the preparation method described in Comparative Embodiment 1; and raw materials not subjected to any process were used as control No. 1 and control No. 2.

The *Ganoderma lucidum* spores No. 1 and the *Ganoderma lucidum* spores No. 2 were from different cultivars, namely *Ganoderma lucidum* cultivar 119 and *Ganoderma lucidum* cultivar Xianzhi No. 2.

2. Content determination: the *Ganoderma lucidum* total triterpenes contains a variety of triterpenoids, and the content of ganoderic acid A is low in the *Ganoderma lucidum* spore powder. By measuring the content of the ganoderic acid A in the raw materials and the *Ganoderma lucidum* spore powder obtained by different preparation methods, and extraction rates, this embodiment verified the ability of the bitter *Ganoderma lucidum* spore powder provided by the present invention in enriching the bitter substances.

By using a ganoderic acid A standard as the reference, the content of the ganoderic acid A in the sample to be tested was detected via HPLC, and the chromatographic conditions were: chromatographic column: Aglient ZORBAX SB-Aq C18 (4.6 mm×250 mm, 5 μm) chromatographic column; and conducting gradient elution at a flow rate of 1.0 mL/min by using acetonitrile (A)-(0.1%) aqueous acetic acid solution (B) as a mobile phase. The gradient elution was conducted with acetonitrile (A)-(0.1%) aqueous acetic acid solution (B). 3D data was acquired at a detection wavelength of 190 nm-400 nm. Data analysis was conducted for 252 nm, the column temperature was 30° C., and the injection volume was 10 μL.

3. Test results: the content of the ganoderic acid A in each sample was shown in Table 2, and according to differences of *Ganoderma lucidum* spore raw materials, the obtained chromatograms were plotted into fingerprint chromatograms, i.e., FIGS. 4 and 5.

TABLE 3

Contents of ganoderic acid A component in respective samples

| Sample | Content of Ganoderic Acid A (μg/g) |
|---|---|
| Control No. 1 | 94.68 |
| Sporoderm-disrupted Ganoderma lucidum spore powder No. 1 | 162.1 |
| Bitter Ganoderma lucidum spore powder No. 1 | 642.69 |
| Control No. 2 | 346.48 |
| Sporoderm-disrupted Ganoderma lucidum spore powder No. 2 | 526.65 |
| Bitter Ganoderma lucidum spore powder No. 2 | 1693.73 |

As shown in Table 2, after the *Ganoderma lucidum* spore raw material No. 2 was processed by the preparation method as provided by the present invention, the content of the ganoderic acid A in the *Ganoderma lucidum* spore powder reached 1,693.73 μg/g, which was 5-6 times higher than that of the raw material; and after the *Ganoderma lucidum* spore raw material No. 1 was processed by the preparation method provided by the present invention, the content of the ganoderic acid A in the *Ganoderma lucidum* spore powder reached 642.69 μg/g, which was also 5-6 times higher than that of the raw material. It can be seen that, conducting extraction on the *Ganoderma lucidum* spore raw materials of different sources by using the preparation method provided by the present invention can significantly improve the content of the bitter substances of the *Ganoderma lucidum* spores compared with the conventional sporoderm disruption method, and thus the preparation method provided by the present invention has a strong enrichment ability.

The content of the ganoderic acid A was relatively low in *Ganoderma lucidum* spores, and the content of the ganoderic acid A in the *Ganoderma lucidum* spore powder prepared by the conventional preparation method was lower or even approaching zero. The content of the ganoderic acid A in the *Ganoderma lucidum* spore powder was difficult to reach the effective dose and thus the *Ganoderma lucidum* spore powder could not give play to the pharmacological effects it would have. The method for preparing bitter *Ganoderma lucidum* spore powder as provided by the present invention can effectively enrich the bitter substances contained in the *ganoderma* spores, increase the content of the bitter substances, and further makes the content of the bitter substances reach the effective dose to give play to the pharmacological effects, thereby making the bitter *Ganoderma lucidum* spore powder prepared by the present invention have more extensive pharmacological effects.

Figure 4:
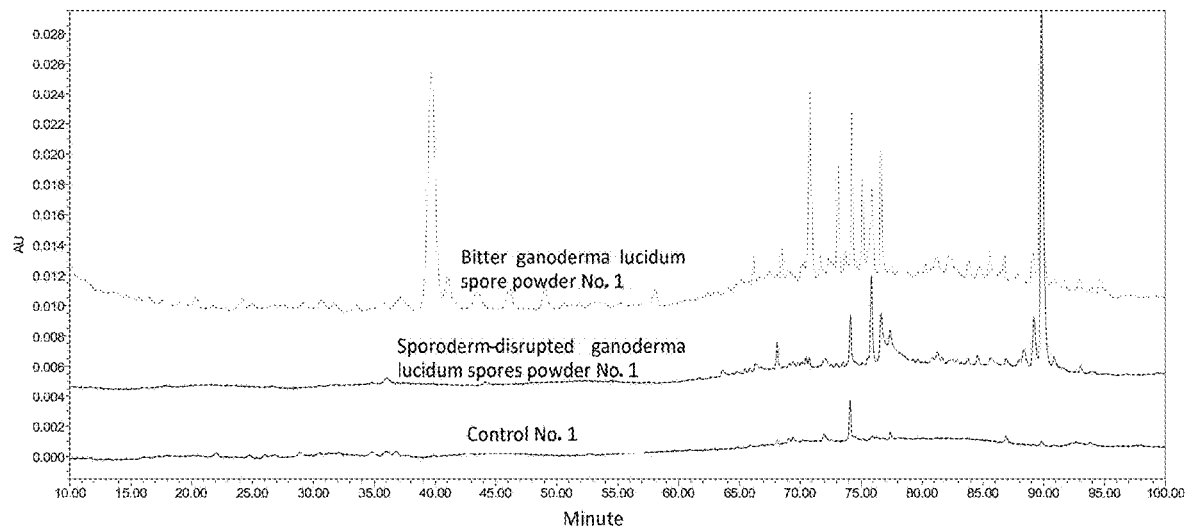
FIG. 4 is comparison of HPLC fingerprint chromatograms of respective *Ganoderma lucidum* spores obtained in Embodiment 10 by using *Ganoderma lucidum* spores No. 1 as raw materials.
Figure 5:
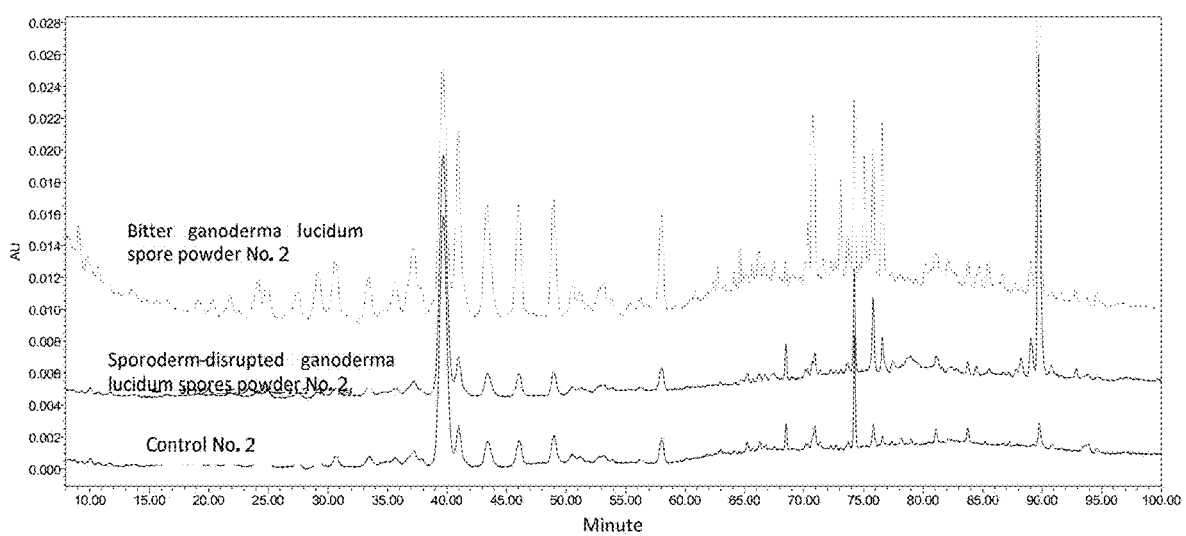
FIG. 5 is comparison of HPLC fingerprint chromatograms of respective *Ganoderma lucidum* spores obtained in Embodiment 10 by using *Ganoderma lucidum* spores No. 2 as raw materials.

After assay determination of the triterpene component in the intermediate was conducted, the HPLC finger-print chromatogram of the intermediate was shown in FIGS. 4 and 5. The results showed that, for each of the sporoderm-disrupted *Ganoderma lucidum* spore powder No. 1 (conventional sporoderm-disruption method) and the control No. 1 (*Ganoderma lucidum* spores not subjected to sporoderm disruption), the retention time was between 10-50 min, and there was substantially no obvious peak when the detection wavelength was 252 nm; however, for the bitter *Ganoderma lucidum* spore powder No. 1 (prepared by the method of the present invention), a plurality of peaks could be observed in the processing intermediate material at 10-50 minutes. At the same time, the peak area of each peak was also increased significantly between 60-90 min. It could be seen from three sets of HPLC fingerprint chromatograms (FIG. 5) obtained from the *Ganoderma lucidum* spores No. 2 that, for the sporoderm-disrupted *Ganoderma lucidum* spore powder No. 2 (conventional sporoderm-disruption method) and the control No. 2 (*Ganoderma lucidum* spores not subjected to sporoderm disruption), the retention time is between 10-50 min, an absorption peak could also be observed at a wavelength of 252 nm; however, for the bitter *Ganoderma lucidum* spore powder No. 2 (prepared by the method of the present invention), the component at 10-50 min was effectively enriched, a plurality of peaks could be detected, and meanwhile the peak area between 60-90 min was also significantly increased. It can be seen that, the preparation method provided by the present invention can effectively enrich the total triterpene substance of *Ganoderma lucidum* relative to the conventional sporoderm-disruption method, i.e., effectively enriching the bitter substances contained in the *Ganoderma lucidum* spores.

Embodiment 12

1 part by weight of the bitter *Ganoderma lucidum* spore powder prepared in Embodiment 1 and 5-10 parts by weight of purified water were taken and mixed to obtain a clear solution, which was a bitter *Ganoderma lucidum* spore oral liquid.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A drug or health care product comprising a powder of *Ganoderma lucidum* spores, wherein the drug or health care product has a dosage form selected from granules, tablets, powders, capsules, oral liquids, injections, sprays, aerosols, power aerosols, lotions, liniments, ointments, emulsions, patches, eye drops, nasal drops, suppositories, pills, microsphere preparations, tinctures, sustained release preparations, controlled release preparations or targeting preparations, wherein the powder of *Ganoderma lucidum* spores has been prepared by a method comprising impurity removal, ice bathing and heat extraction, filtration through a microfiltration membrane, sterilization at low pressure, and sporoderm disruption, wherein the powder of *Ganoderma lucidum* spores comprises triterpenes in a range of between 5 to 8 percent by mass, and wherein the powder of *Ganoderma lucidum* spores comprises polysaccharides in a range of between 6 to 10 percent by mass.

2. The drug or health care product according to claim 1, further comprising a pharmaceutically acceptable auxiliary material.

3. The drug or health care product according to claim 1, wherein a content of the bitter *Ganoderma lucidum* spore powder is no less than 80%.

4. The drug or health care product according to claim 3, further comprising a pharmaceutically acceptable auxiliary material.

* * * * *